US010258036B2

(12) United States Patent
Humbert et al.

(10) Patent No.: US 10,258,036 B2
(45) Date of Patent: *Apr. 16, 2019

(54) **EXTRACT OF *EUODIA SUAVEOLENS* SCHEFF, REPELLENT COMPOSITIONS AND USE THEREOF**

(71) Applicant: CHARABOT, Grasse (FR)

(72) Inventors: Marina Humbert, Grasse (FR); Sophie Lavoine-Hanneguelle, Mouans Sartoux (FR)

(73) Assignee: CHARABOT, Grasse (FR)

( * ) Notice: Subject to any disclaimer, the term of this patent is extended or adjusted under 35 U.S.C. 154(b) by 405 days.

This patent is subject to a terminal disclaimer.

(21) Appl. No.: 15/077,313

(22) Filed: Mar. 22, 2016

(65) Prior Publication Data

US 2016/0198706 A1 Jul. 14, 2016

Related U.S. Application Data

(60) Continuation of application No. 13/912,640, filed on Jun. 7, 2013, now Pat. No. 9,320,273, which is a division of application No. 13/256,078, filed as application No. PCT/FR2010/000209 on Mar. 12, 2010, now Pat. No. 8,481,088.

(30) Foreign Application Priority Data

Mar. 12, 2009 (FR) ..................................... 09 01145

(51) Int. Cl.
| | |
|---|---|
| *A61K 36/00* | (2006.01) |
| *A61K 36/754* | (2006.01) |
| *A61K 31/34* | (2006.01) |
| *A01N 43/12* | (2006.01) |
| *A01N 65/00* | (2009.01) |
| *A01N 65/36* | (2009.01) |

(52) U.S. Cl.
CPC .............. *A01N 43/12* (2013.01); *A01N 65/00* (2013.01); *A01N 65/36* (2013.01); *Y02A 50/328* (2018.01)

(58) Field of Classification Search
None
See application file for complete search history.

(56) References Cited

U.S. PATENT DOCUMENTS

| 4,552,755 A | 11/1985 | Randen |
| 4,816,256 A | 3/1989 | Randen |
| 5,843,215 A | 12/1998 | Whalon et al. |
| 6,524,605 B1 | 2/2003 | Coats et al. |
| 2006/0183663 A1 | 8/2006 | Lentsch et al. |
| 2007/0154504 A1 | 7/2007 | Coats et al. |

OTHER PUBLICATIONS

Brophy et al. (1985) Flavour and Fragrance Journal, vol. 1, 17-20. (Year: 1985).*
Website document entitled: "HealthyLifeDigest: Green Mosquito Repellants, Repel Mosquito naturally!" Feb. 25, 2009. Available at: http://healthylifedigest.blogspot.com/2009/02/green-mosquito-repellants-repel.html. (Year: 2009).*
International Search Report of PCT/FR2010/000209, dated Jul. 5, 2010.
Anonymous, "Evodia suaveolens Schell—Zodia," Jul. 20, 2008, http://anekaplanta.wordpress.com/2008/07/30/evodia-suaveolens-scheff-zodia, Retrieved on Oct. 6, 2009.
Anonymous, "Zodia—Mosquito Repellent Plant," Sep. 21, 2007, http://web.archive.org/web/20070921115901/http://sl.biotrop.org/product_detail.php?id_produk=9, Retrieved on Oct. 6, 2009.
Stetter, Hermann et al. "Synthesis of evodone and menthofuran," Chemische Berichte, Oct. 30, 1959, vol. 93, pp. 603-607.
Yaghmai, Mohammad Shahram et al. "The essential oil of Dracocephalum kotschyi Boiss," Flavour and Fragrance Journal, 1988, vol. 3, pp. 33-36.
Brophy et al., "The Volatile Oils of Euodia hortensis forma hortensis" (1985) Flavour and Fragrance Journal, vol. 1, pp. 17-20.
Weidenhamer et al., "Allelopathic Potential of Menthofuran Monoterpenes From Calamintha Ashei", Journal of Chemical Ecology, vol. 20, No. 12, 1994, pp. 3345-3359.
Makoto, "Dissertation Abstracts International", vol. 47, No. 8, Feb. 1987, p. 3363-B (2 pages).
Website document entitled: HealthyLifeDigest: Green Mosquito Repellents, Repel Mosquito naturally, Wednesday, Feb. 25, 2009. Available at: http://healthylifedigest.blogspot..com/2009/02/green-mosquito-repellents-repel.html (7 pages).
Srikrishna et al., "A simple synthesis of (±)-evodone", Indian Journal of Chemistry, vol. 28B, Oct. 1989, p. 852.

* cited by examiner

*Primary Examiner* — Christopher R Tate
*Assistant Examiner* — Russell G Fiebig
(74) *Attorney, Agent, or Firm* — Westerman, Hattori, Daniels & Adrian, LLP

(57) ABSTRACT

The invention relates to an extract of *Euodia suaveolens* Scheff. The invention is characterized in that the extract is obtained from the airborne portions of the plant by means of at least one extraction step using an organic or hydro-alcoholic solvent, and in that it comprises evodone at a concentration of between 0.1 and 35% by weight of the total weight of the extract, and in that it has an insect repellent activity. The invention also relates to a repellent composition, characterized in that it comprises, in a cosmetically acceptable medium, evodone at a concentration of between 0.1 and 25% by weight of the total weight of the composition, and to the use of evodone as an active agent for repelling insects, in particular mosquitoes and more particularly the European/Mediterranean mosquitoes of the *Aedes aegypti* species.

22 Claims, 3 Drawing Sheets

EXTRACT OF *EUODIA SUAVEOLENS* SCHEFF, REPELLENT COMPOSITIONS AND USE THEREOF

CROSS REFERENCE TO RELATED APPLICATIONS

This application is a continuation of U.S. application Ser. No. 13/912,640 filed Jun. 7, 2013, which is a divisional of U.S. application Ser. No. 13/256,078 filed Sep. 12, 2011, which is a U.S. national stage of PCT/FR2010/000209 filed Mar. 12, 2010, the contents of each of which are hereby incorporated by reference herein in their entirety.

The present invention relates to an extract obtained from airborne portions of the plant *Euodia suaveolens* Scheff, repellent compositions, as well as their use for repelling insects, in particular mosquitoes and more particularly the European-Mediterranean mosquitoes of the *Aedes aegypti* species.

Environmental, climatic and societal changes in Europe and countries of the South influence the distribution and dynamics of pathogens and their vectors, thus contributing to the emergence/re-emergence of diseases such as malaria, dengue fever or Nile virus, with considerable economic and health impacts.

The fight against vectors is the best large-scale prevention strategy applicable to most tropical diseases transmitted by insects, especially those transmitted by mosquitoes. Indeed, for some diseases such as malaria, yellow fever, encephalitis, dengue fever, Chagas disease and, more recently, chikungunya, there is no immediately effective vaccine or curative means.

Thus, the strategies used to reduce the incidence of vector-borne diseases have focused on the elimination or control of vector populations by chemical and biological means, such as insecticides, and on personal protections, primarily in the form of repellent products. The latter are notably subject to renewed interest in the field of public health. The use of repellents can also become an effective personal protective measure in those areas where the biology and behavior of vectors make the use of conventional methods such as impregnated materials, or the spraying of insecticides, less appropriate, such as in South East Asia or in the Indian Ocean.

However, insecticides are known to be toxic and can irritate the respiratory tract, eyes and skin, or cause nervous system or gastrointestinal disorders, or also accumulate in the fatty tissue of humans.

Therefore, it is preferred to use repellents, which are synthetic or natural chemicals, capable of causing negative chemotropism in pests. Repellents are also known as insectifuges or "mosquito-repellents". They do not generally kill the insects, but keep them away. Repellents alter the insect's orientation ability, thus diverting it from its potential target.

Many stimuli (visual, thermal, olfactory) are involved when insects locate their prey. Thus, to date, the exact mechanism acting in repellents is not yet known. In addition, few efficacy and long-term toxicity studies have been performed on repellents.

Essential oils are generally known to have a lower repellent power than synthetic products.

The efficacy of a repellent depends on its concentration, the target insect, the excipient (volatility, extended-release, . . . ), but also on many other environmental factors.

Chemical repellents include, in particular, products based on DEET (N,N-diethyl-3-methylbenzamide or N,N-diethyl-m-toluamide) with the following chemical structure:

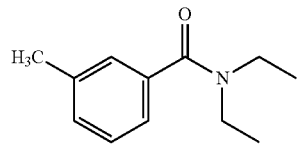

This synthetic compound is known as the most commonly used and most effective repellent on the market. Approximately 200 million people use DEET each year and more than 8 billion doses have been applied over the last 50 years. It has been shown that DEET blocks the electrophysiological response of the insect's sensory neurons, which are involved in olfactory attraction. It confers a protection period generally ranging from 2 to 8 hours depending on the compounds with which it may be associated in the products, and more specifically depending on its concentration. For example, it confers a protection period of more than 5 hours for DEET at a dose of 23.8 percent, according to a study carried out in the laboratory on *Aedes aegypti* (Fradin M S, Day J F "Comparative efficacy of insect repellents against mosquito bites", New England Journal of Medicine, 2002).

However, DEET has an unpleasant and persistent odor, a greasy texture on the skin, is irritating to the eyes and mucous membranes, and also has an aggressive effect on certain plastics (watches, glasses). Thus, even though it has been re-registered by the Environmental Protection Agency, it can be toxic at a concentration greater than 30%, especially in children under the age of 12, pregnant women and nursing mothers. In addition, its toxicity being related to skin permeability, since 30% of a dose of DEET is absorbed through the skin, and to its storage capacity in the skin, since urinary excretion represents 10 to 15% of its dose, it may be advisable not to use it at a concentration greater than 30%.

However, a concentration of DEET below 30% has little efficacy against mosquitoes in individuals over 12 years of age, as its active concentration is 30 to 50%.

Recently, studies have shown that DEET might increase the concentration of acetylcholine in the synaptic cleft by inhibiting acetylcholinesterase (Vincent Corbel et al. "Evidence for inhibition of cholinesterases in insect and mammalian nervous system by the insect repellent DEET". BMC Biology, August 2009). Acetylcholinesterase is a key enzyme in the transmission of nerve impulses. Once information has been transmitted, the chemical mediator, acetylcholine, degrades. Inhibition of acetylcholinesterase leads to an accumulation of acetylcholine, which maintains permanent transmission of nerve impulses, which may lead to muscle tetany.

Although serious side effects nevertheless remain exceptional and are often linked to an overdose or overuse, this discovery once again poses the issue of safety in the use of DEET and raises the hypothesis that DEET represents a risk of nervous toxicity in the human species.

Also known is icaridin or KBR3023 or 1-methylpropyl-ester, which is a synthetic chemical repellent, having the following chemical structure:

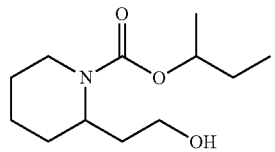 [SMILES: CCC(C)OC(=O)N1CCCCC1CCO]

It is described as having an efficacy comparable to that of DEET, but at lower concentrations (19.2% icaridin vs. 30% DEET). Icaridin is almost odorless, does not cause skin irritation, although it produces only a slight irritation of the eye, and has no adverse effect on plastics. The use of icaridin in effective amounts of between about 20 and 30% is however not recommended in children under 30 months and pregnant women.

Synthetic repellents available on the market also include IR3535 or ethyl-butyl-acetyl-aminopropionate, having the following chemical structure:

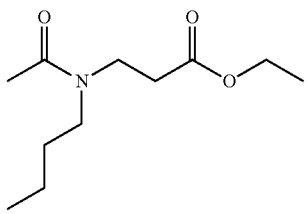

The active concentration of IR3535 is between 20 and 35%. It is the only chemical repellent not prohibited for pregnant women. Its acute and chronic toxicities are low. According to the EPA, on the basis of its use for 20 years in Europe with no significant adverse effect, the risk is considered to be minimal to nil. However, its effectiveness is found to be lower than that of DEET, with an average efficacy of 4 hrs for IR35/35 above 20%.

There are other known repellents, such as citriodiol or p menthane 3.8 diol (a natural *Eucalyptus* extract), neem, or geraniol, which are natural extracts available on the market. These prove to be effective and can provide protection which generally has a maximum persistence of 6 hours for citriodiol, to 2 hours.

Other natural extracts such as extracts of *Spilanthes* (*Acmella oleracea*) or Sichuan pepper (*Zanthoxylum piperitum*), may also prove to be effective as repellents. However, the active ingredients of *Spilanthes* and Sichuan pepper are alkylamides, which may be skin irritants at concentrations of the order of 15 to 20%.

Natural repellents also include oils and essential essences, extracted by steam distillation and expression, in particular those of geranium, garlic, lavender, or also citronella which, however, are not considered to be very effective, and provide protection with a persistence of about 2 hours to 30 minutes, or even less, depending on the wind and outside temperature. They require much more frequent applications than synthetic repellents to maintain an effective level of protection. They can also be too odorous. Furthermore, the pure essential oil of *Euodia suaveolens* Scheff appears, according to tests conducted by the applicant, to be effective but highly volatile and above all highly odorous and therefore not usable as such.

In general, there is a real demand for the provision of products or preparations, which would advantageously be of natural origin, much less harmful to human health, and biodegradable. In the present context, particularly in the context of biocide regulation, there is a need to find a natural or synthetic repellent, which would be less toxic and less irritating, at least as effective as DEET and icaridin, and would not have the adverse effects of prior art repellents.

*Euodia suaveolens* Scheff is a plant of the Rutaceae family, better known as Zodia, or also Tanaman Zodia. Approximately 150 genera of *Euodia*, and perhaps more than 1500 species, are described in the literature, among which *Euodia suaveolens* Scheff, although it is referred to as *Evodia* in the scientific literature dealing with this genus. This Indonesian plant originates from the region of Irian, in Western Papua New Guinea, where it is known under local names such as Halau nyamuk, Durian Hantu Hutan or Sukang or Sungei. It is also found on the island of Java and other Asian countries. *Euodia suaveolens* Scheff is a bushy evergreen shrub that can reach a height of between 0.3 and 3 meters, in general 0.75 meters. Its thin leaves, of a light green color and with a shiny, waxy and smooth aspect, are simple and linear, long-stalked and may reach a length of 20-30 cm for mature foliage. Their central vein protrudes from the underside. They have a bitter taste. Their flowers are pale yellow, arranged in clusters and flourish in the summer. This plant gives off a strong aromatic odor.

Inhabitants of areas where this plant is grown have used *Euodia suaveolens* Scheff for many years in traditional medicine. In particular, its leaves are used to fight malaria and other diseases vectorized by mosquitoes, such as dengue. It also appears that wounds resulting from attacks by infected mosquitoes heal faster when placed in contact with the foliage of this plant.

The repellent activity of the leaves of *Euodia suaveolens*, after the skin has been rubbed with them, against dengue carrying mosquitoes, has also been reported (Agus Kardinan, 2005, Services Laboratory, Seameo Biotrop, Zodia—Mosquito repellent plant). The gas chromatography analysis of the essential oil obtained from leaves of this plant, conducted by the Balai Penelitian Tanaman Rempah dan Obat (Baittro) revealed the presence of 46% of linalool, having the following chemical structure:

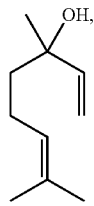

and 13.26% of alpha-pinene having the following chemical structure:

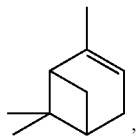

which are molecules considered to be repellents by some researchers. It is also reported in the literature that, in the opinion of other researchers, this repellent activity could be due to evodiamine, having the following chemical structure:

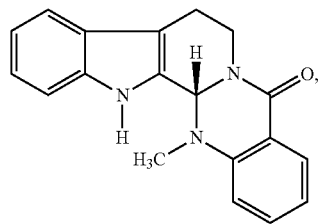

and rutaecarpine, having the following chemical structure:

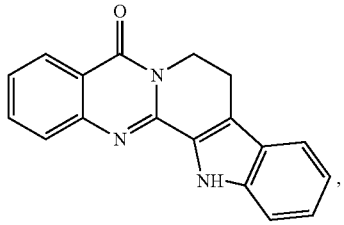 [SMILES: O=c1c2ccccc2nc2n1CCc1c-2[nH]c2ccccc12]

which are present in the leaves of *Euodia suaveolens*.

In spite of these teachings, it should be noted that there has not been any report, or even suggestion, concerning a repellent that would be effective against insects, in particular mosquitoes, from extracts of *Euodia suaveolens* Scheff, in particular those not containing an effective amount of linalool, alpha-pinene, or evodiamine or also rutaecarpine.

In consideration of the above, a problem addressed by the invention is that of developing a natural or synthetic repellent, capable of repelling insects as effectively as a known synthetic chemical insect repellent, and which does not have the side effects observed in the prior art.

Thus, with a view to meeting this need, the applicant has unexpectedly discovered that extracts derived from *Euodia suaveolens* Scheff that do not contain linalool, alpha-pinene, evodiamine and/or rutaecarpine or, at least not in an effective amount, show remarkable repelling activity against insects, in particular mosquitoes and, particularly, European/Mediterranean mosquitoes of the *Aedes aegypti* species, thus providing a new response in terms of protection against insects, while at the same time preserving the environment and human health. The applicant has also specifically identified the active agent responsible for such a repellent activity.

The extract and repellent agent according to the invention offer the following advantages over the prior art:
the extract is natural;
the extract and active agent have a more efficient repellent activity against insects, in particular against mosquitoes and particularly against European/Mediterranean mosquitoes of the *Aedes aegypti* species, than prior art natural extracts;
the extract and active agent, depending on their concentration, have a repellent activity which is as effective as chemical repellents and more particularly DEET;
the active agent can be used at a low dose; and
the extract and compositions comprising said active agent do not have the adverse effects of chemical insecticides and insect repellents.

A first object of the invention is therefore to provide an extract of *Euodia suaveolens* Scheff, characterized in that it is obtained from the airborne portions of the plant by means of at least one extraction step with an organic or hydro alcoholic solvent and in that it comprises evodone at a concentration of between 0.1 and 35% by weight of the total weight of the extract, and in that it has an insect repellent activity.

In addition, a second object of the solution of the invention is to provide a repellent composition, characterized in that it comprises, in a cosmetically acceptable medium, evodone at a concentration of between 0.1 and 25% by weight of the total weight of the composition.

A third object the invention is also to use evodone as an active agent for repelling insects, in particular mosquitoes and more particularly European/Mediterranean mosquitoes of the *Aedes aegypti* species.

The invention and benefits derived therefrom will be better understood after reading the following non-limiting description and embodiments with reference to the accompanying figures, in which.

Figure 4:
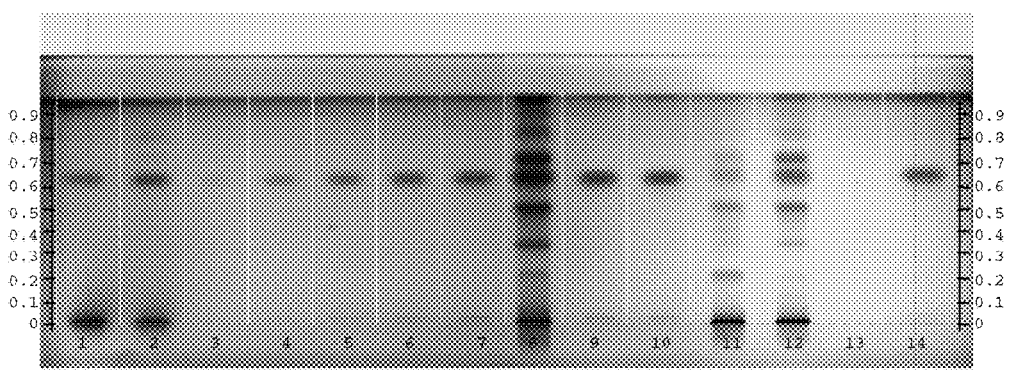
Figure 5:
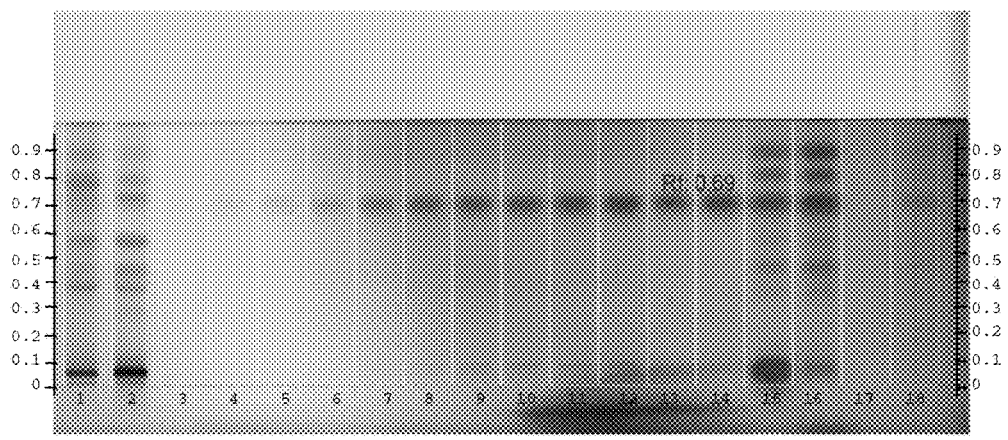

FIG. 4 is a reading of a HPTLC chromatogram after visible light development, showing different extracts of *Euodia suaveolens* Scheff and revealing the presence of evodone in the extracts according to the invention; and FIG. 5 is a reading of a HPTLC chromatogram after visible light development, showing different extracts of *Euodia suaveolens* Scheff and revealing the presence of evodone in the extracts according to the invention.

In this description, unless otherwise specified, it is understood that when a concentration range is given, it includes the upper and lower bounds of said range, and that the concentration is given by weight relative to the total weight of the composition or extract concerned.

The extract of *Euodia suaveolens* Scheff according to the invention is isolated from the airborne portions of the plant.

By airborne portions of the plant is meant the stems, leaves and flowers of the plant. These can be used fresh or dried, advantageously dried.

To obtain the extract according to the invention, the airborne portions of *Euodia suaveolens* Scheff are advantageously harvested, dried and coarsely ground.

At least one extraction step is then performed using organic or hydro-alcoholic solvents. This extraction step is different from an extraction step for the production of an essential oil or essence, which is obtained strictly by steam distillation or expression.

The extraction is advantageously repeated several times, for example 3 times.

It is performed with a plant/extraction solvent ratio, by weight/volume, between about 1/1 and about 1/20, for example 1/5 or 1/10.

According to the invention, the temperature of the extraction solvent is greater than or equal to about 15° C., or room temperature. Advantageously, the maximum extraction temperature is the reflux temperature of the extraction solvent. For example, the extraction is carried out at 75° C. with ethanol.

According to the invention, the extraction is advantageously dynamic and is performed under stirring.

According to the invention, the extraction time is between 30 minutes and 5 hours for each extraction step, for example 3 or 4 hours.

Non-limiting examples of organic solvents of the invention include alkanes, ether-oxides, esters, alcohols, halogenated hydrocarbons, carbon dioxide in the supercritical state.

The organic solvent according to the invention is preferably selected from pentane, hexane, heptane, octane, cyclohexane, tetrahydrofuran, dioxane, diethyl ether, ethyl acetate, isopropyl acetate, methanol, ethanol, propanol, isopropanol, butanol, methyl ethyl ketone, dimethyl ketone, methyl isobutyl ketone, dichloromethane, dimethyl carbonate or carbon dioxide in the supercritical state or a mixture of the above-mentioned solvents, preferably hexane and ethanol.

Advantageously, the organic solvent is selected from organically produced solvents, for example alcohols and carbon dioxide in the supercritical state.

According to the invention, the hydro-alcoholic solvent, for example, is an ethanol/water dilution solvent with a ratio of 80/20 by volume.

In the preparation of an extract according to the invention, a separation of the solid phase from the liquid phase is then carried out. The solid portions of the plant are thus separated from the liquid extraction juice by plate filtration or centrifugation, pressing.

The thus obtained filtrate is then concentrated by evaporation, to yield a more or less concentrated extract, if appropriate until total evaporation of the extraction solvent.

Advantageously, the filtrate can be concentrated by vacuum evaporation.

The dark green-brown concentrated extract can then be bleached or refined using activated carbon, or acidic or clayey earths, or molecular distillation or extraction with carbon dioxide in the supercritical state or codistillation.

The extract according to the invention can then be purified. It can be purified by any technique known to one skilled in the art, such as, for example, liquid phase-liquid phase extraction between 2 immiscible solvents, absorption onto a carrier such as silicate or an ion exchange resin, precipitation or crystallization.

The mass yield of the extract is between about 1% and about 25% of the dry matter involved, for example about 15%.

According to the invention, different types of extractions can be performed, such as maceration (static extraction at room temperature), hot static extraction, decoction, leaching.

According to an advantageous embodiment of the invention, from a quantitative point of view in terms of yield, a Soxhlet extraction or dynamic extraction, maceration, static hot extraction, ultrasonic extraction or microwave extraction with ethanol at a concentration greater than about 80%, for example 80%, 96% or 97%, is carried out.

After purification, the extract according to the invention can be dried by total evaporation of the solvent and then dissolution in a compatible and cosmetically acceptable solvent.

Another feature of the extract is that it does not contain linalool, alpha-pinene, or evodiamine, rutaecarpine, or at least not in an effective amount according to the prior art. Even though these compounds are present in the plant, the extract or oleoresins obtained from this plant contain only a small amount of linalool and alpha-pinene and neither evodiamine nor rutaecarpine.

Furthermore, the extract according the invention has a zero or very small titer of these molecules, for example a content of less than 1%, preferably less than 0.1%, and therefore contains only trace amounts of these molecules. Indeed, linalool and alpha-pinene are removed, in particular, during the organic or hydro-alcoholic extraction of the extract according to the invention. These molecules are driven by the distillation of the solvent and are diluted by concentrating the extract. For evodiamine and rutaecarpine, the solvent used for the extraction according to the invention is not selective for these types of alkaloid structures. The extract according to the invention, when tested on European/Mediterranean mosquitoes of the Aedes aegypti species, therefore no longer contains, or contains only trace amounts of these four molecules. According to the invention, the properties displayed by such an extract are not attributable to the presence of such substances.

The extract according to the invention, which, in itself, is a new product, however contains non-volatile compounds such as flavonoids, for example glycosylated flavanols such as rutine or 3 O-rutinosylquercetol, flavonols such as kaempferol and isorhamnetin or methyl-3-quercetin, a flavone, such as a derivative of apigenine, for example vitexin or vitexin 2"O rhamnoside, as well as volatile compounds such as bicyclic lactones, in particular evodone or (6S)3-6 dimethyl 6,7 dihydro 5H benzofuran-4-one, menthalactone or mintfuranone or 3,6-dimethyl-5,6,7,7a-tetrahydro-4H-1-benzofuran-2-one, aromacurcumene, and fatty acids, in particular of the acidic, palmitic or oleic type.

In particular, the extract of the invention contains a titer of evodone, having the following chemical structure:

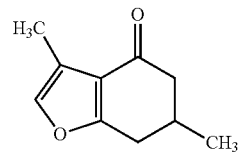

Evodone is an oxygenated monoterpene, that is, a benzofuranone derived from menthofuran. Its description can be found, in particular, in Euodia hortensis (Rutaceae). The plant Calamintha ashei (Lamiaceae) also contains oxygenated monoterpenes such as evodone, caryophyllene, menthofuran, and calaminthone. These compounds have been studied for their allelopathic properties for the inhibition of the seeds of certain species such as Lactuca sativa and Schizachyrium scoparium. A mixture of these terpenes appears to inhibit seed germination, but the individual compounds do not seem to have a significant activity.

The synthesis of evodone can be performed from 5-methylcyclohexan-1,3-dione in the presence of chloroacetone (A. Srikrisma and G. Veera Raghava Sharma, "A simple synthesis(+/−) evodone", Indian journal of Chemistry, 1989, p. 852). 99% pure evodone (racemic mixture) was thus obtained.

The evodone titer of the extract according to the invention advantageously corresponds to a concentration of between about 0.1 and 35% by weight of the total weight of the extract, preferably between 0.2 and 5%.

For example, a crude, unrefined oleoresin according to the invention may comprise between 0.1 and 35% of evodone, for example 0.8% for an unrefined crude extract, and 20.16% when the codistilled oleoresin is taken up in hexane, and a codistilled refined extract may include between 0.1 and 20% of evodone, for example 2%.

As shown in FIGS. 1, and 3 to 5, evodone is present in an extract of Euodia suaveolens Scheff according to the invention.

Figure 1:
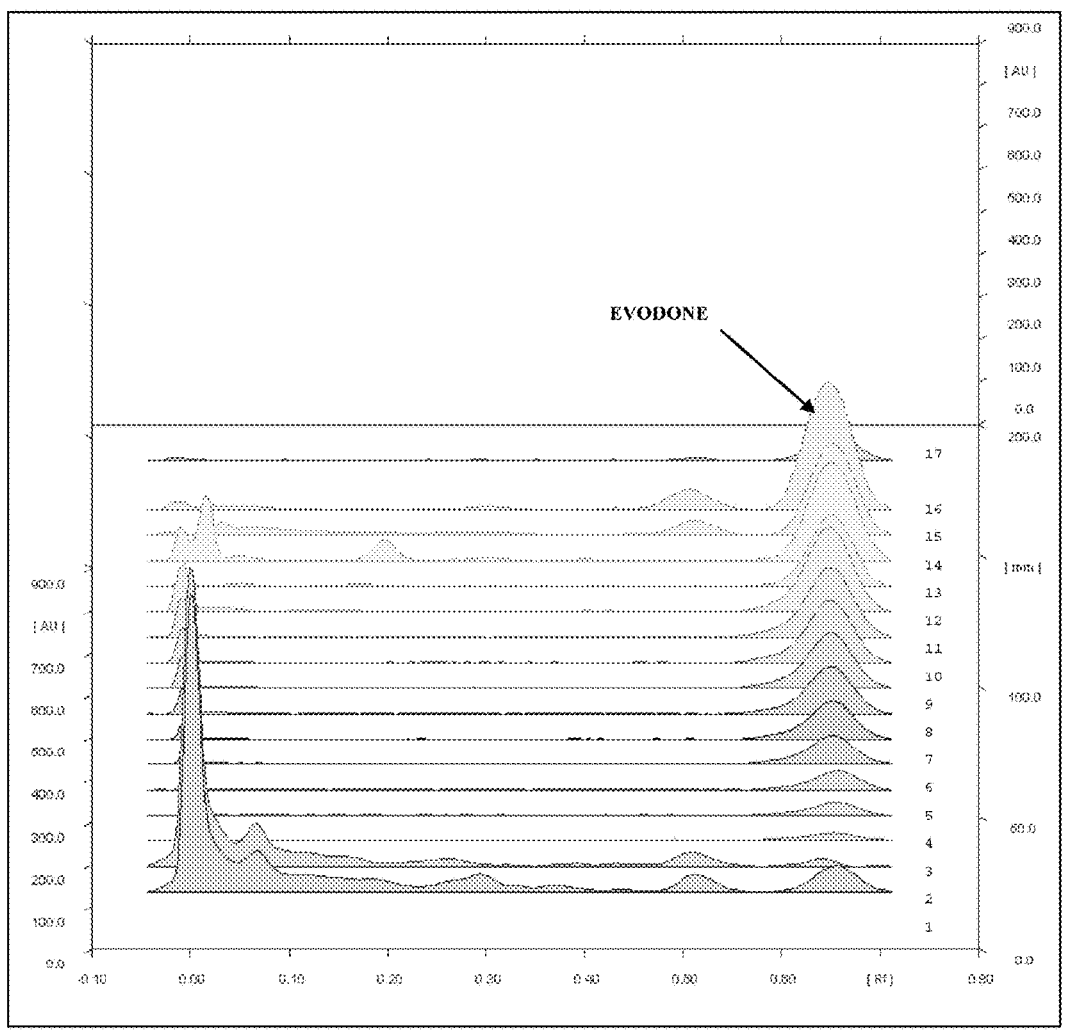
FIG. 1 is a 3D chromatogram obtained by high-performance thin layer chromatography (HPTLC) at 280 nm using a scanner, revealing the presence of evodone in different extracts of *Euodia suaveolens* Scheff.

In FIG. 1, chromatograms 3 to 14 represent the deposited evodone standard at the same concentration and different volumes, and are characterized by the presence of a peak having a baseline (front ratio) of 0.69 for this mobile phase in this particular analysis case. It is observed that the same evodone-characteristic peak is present in chromatograms 1, 2, 15, 16, 17 pertaining to extracts of Euodia suaveolens Scheff, namely, respectively, in an oleoresin obtained from fresh leaves, an oleoresin obtained from dry leaves, a formulation based on a codistilled extract with an evodone content of 0.3%, another formulation based on a codistilled extract with an evodone content of 2.36%, and codistilled oleoresin taken up in hexane.

Furthermore, analysis of the essential oil of Euodia suaveolens Scheff, by comparing the essential oil with the oleoresin extracted according to the invention, reveals various compounds identified by gas chromatography coupled with mass spectrometry.

The Table below shows some of the compounds mentioned above and described by some authors as being responsible for the repellent activity (including alpha pinene and linalool). This Table shows that, based on the obtained results, alpha pinene and linalool, in particular, are not present in the oleoresin extracted according to the invention. However, the oleoresin extracted according to the invention retains a strong repellent activity against mosquitoes.

| Compounds | GC/FID content in the analyzed essential oil | Theoretical content of compounds in the oleoresin extracted according to the invention | Content of compounds analyzed in the oleoresin extracted according to the invention, in GC/FID |
|---|---|---|---|
| alpha pinene | 0.12% | 0.0086% | not detected |
| Limonene | 18.77% | 1.13% | not detected |
| Linalool | 0.08% | 0.00480% | not detected |
| Menthofuran | 31.30% | 0.28% | not detected |
| Limonen 10 ol | 6.21% | 0.38% | 2.28% |

For information, the theoretical levels given in the Table have been extrapolated from analyses of the essential oil. Based on this data, it is indeed possible to determine the theoretical contents of these compounds in the plant, and then, in the oleoresin extracted according to the invention.

However, the fact that the oleoresin according to the invention is obtained by alcoholic extraction followed by concentration, should be taken into account. Thus, when the solvent is evaporated, most of these molecules, which are volatile molecules, are primarily driven by azeotropy, which explains why they are not found in the extract according to the invention.

Figure 2:
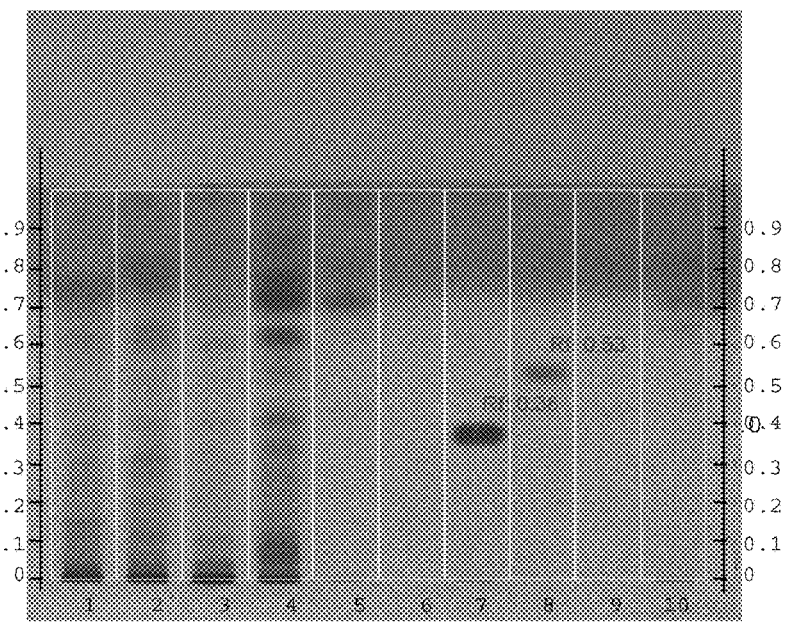
FIG. 2 is a reading at 254 nm before the development of a HPTLC chromatogram, showing different extracts of *Euodia suaveolens* Scheff, revealing the absence, or simply the presence of trace amounts, of rutaecarpine and evodiamine in the extracts according to the invention.

In addition, as shown in FIG. 2, rutaecarpine and evodiamine are not present in the extract of the invention, or are present in trace amounts only.

Specifically, in FIG. 2, different extracts of *Euodia suaveolens* Scheff have been analyzed: lane 1 relates to a concrete obtained by hexane extraction from fresh *Euodia suaveolens* Scheff leaves; lane 2 relates to an absolute obtained by alcohol extraction of the concrete; lane 3 relates to a bleached oleoresin according to the invention; lane 4 relates to an extract according to the invention, bleached by molecular distillation; lane 5 relates to an essential oil of *Euodia suaveolens* Scheff; lane 6 is empty; lane 7 corresponds to the evodiamine standard with a baseline (retardation ratio) of 0.35-0.39, shown to be 0.38 in FIG. 2, under these analytical conditions; lane 8 corresponds to the rutaecarpine standard with a baseline (retardation ratio) of 0.53 under these analytical conditions; lane 9 is empty; and lane 10 corresponds to the evodone standard.

In lanes 3 and 4, the absence of a band with a baseline of 0.53 (retardation ratio) is observed, which is characteristic of the presence of rutaecarpine in these extracts. Thus, the extracts according to the invention deposited in lanes 3 and 4 are free of rutaecarpine. It is also observed in lanes 3 and 4 that there is no significant band having a baseline of 0.38 (retardation ratio), which is characteristic of the presence of evodiamine in these extracts. Only trace amounts are distinguished, which might indicate the presence of traces of evodiamine in the extracts according to the invention.

Figure 3:
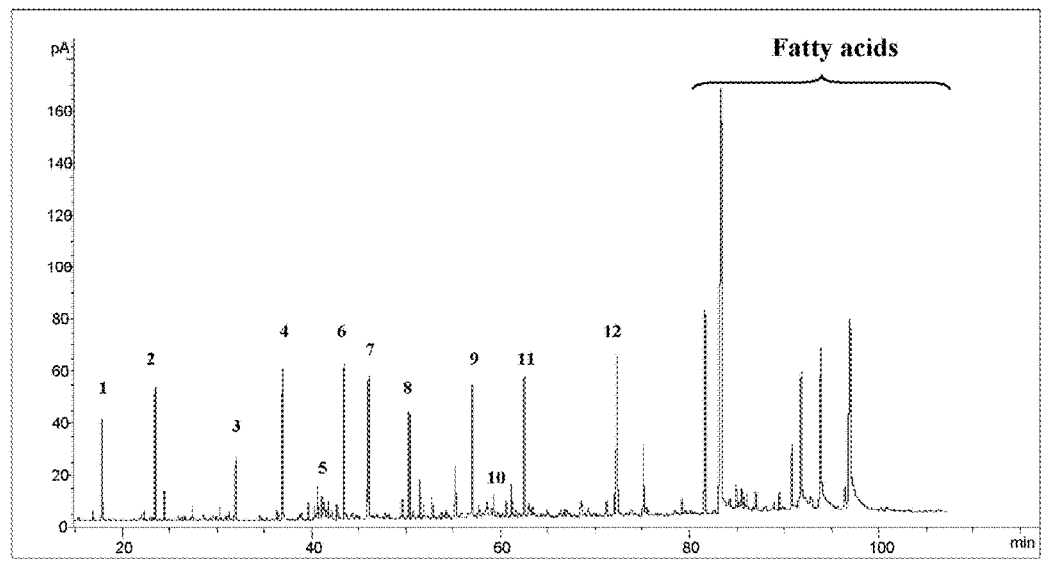
FIG. 3 is a chromatographic profile obtained by gas chromatography with flame ionization detection on a polar column, which characterizes at least the partial composition of an extract of *Euodia suaveolens* Scheff according to the invention.

Furthermore, as shown in FIG. 3, the composition of a bleached ethanol extract of *Euodia suaveolens* Scheff according to the invention has been characterized at least partially by GC/FID chromatography (Agilent Technologies HP 6890) on a polar column (Varian CP8713 CP WAX 52 CB; 50 m×0.25 mm×0.2 mm) following a rise in temperature of 70° C. for 5 min, then of 2° C./min up to 240° C. for 50 min, and for an injected volume of 1 µl. In this extract, peaks that are characteristic of the presence of benzaldehyde (peak 1), carbitol (peak 2), aroma curcumene (peak 3), benzyl alcohol (peak 4), evodone (peak 5), limonene-10-ol or (p-mentha-1,8(10)-dien-10-ol) (peak 6), levojunenol (peak 7), menthalactone isomer 1 (peak 9), menthalactone isomer 2 (peak 10), phytol (peak 12), and peaks that are characteristic of the presence of fatty acids, can be observed.

As illustrated in FIG. 4, HPTLC analyses of evodone and various extracts of *Euodia suaveolens* Scheff according to the invention were carried out: lane 1 relates to an extract of *Euodia suaveolens* Scheff obtained by codistillation on monopropylene glycol in bleached oleoresin; lane 2 relates to an extract obtained by codistillation on monopropylene glycol of a non-bleached oleoresin obtained from fresh *Euodia suaveolens* Scheff leaves; lanes 3 to 7 correspond to the evodone standard; lane 8 relates to a crude unrefined oleoresin obtained by ethanol extraction from fresh *Euodia suaveolens* Scheff leaves; lanes 9 and 10 correspond to the evodone standard; lane 11 relates to a bleached oleoresin obtained by ethanol extraction from dry leaves of *Euodia suaveolens* Scheff; lane 12 relates to a bleached oleoresin obtained by ethanol extraction from fresh leaves of *Euodia suaveolens* Scheff; lane 13 is empty; lane 14 corresponds to the evodone standard.

Thus, the extracts according to the invention that are deposited in lanes 1, 2, 8, 11 and 12 do contain evodone.

As shown in FIG. 5, HPTLC analyses of evodone and various extracts of *Euodia suaveolens* Scheff according to the invention were carried out: lane 1 relates to an unrefined crude oleoresin obtained by ethanol extraction from dry leaves of *Euodia suaveolens* Scheff; lane 2 relates to an unrefined crude oleoresin obtained by ethanol extraction from fresh leaves of *Euodia suaveolens* Scheff; lanes 3 to 14 correspond to the evodone standard; lanes 15 and 16 relate to formulations obtained from codistilled oleoresin extracts; lane 17 is empty; lane 18 relates to hexane extraction of a codistilled oleoresin.

Thus, the extracts of the invention deposited on lanes 1, 2, 15, 16, 18 do contain evodone.

The extract according to the invention is natural. Advantageously, the extract can be certified as organic, using organic extraction solvents such as alcohols or carbon dioxide in the supercritical state.

The extract is biodegradable and non-toxic. Indeed, a toxicity study of an ethanol extract of *Euodia suaveolens* Scheff was performed at a concentration of 100% pure, non-bleached, on six female Sprague Dawley rats, aged 8 weeks and weighing between 186 g and 210 g. The study began after an acclimatization period of 5 days. All factors such as brightness, temperature and humidity were controlled. The results are obtained by comparison with a control group of rats that received dimethyl sulfoxide only. Each rat received a single effective dose of 2000 mg/kg by body weight of the pure extract of *Euodia suaveolens* Scheff, diluted in dimethyl sulfoxide and administered orally, in particular by force-feeding, at a volume of 5 ml/kg of body weight. Based on the results obtained, the extract according to the invention is not toxic. Specifically, it has an LD50 of more than 2000 mg/kg of body weight. According to the OECD 423 directive, the LD50 can be considered to be greater than 5000 mg/kg by bodyweight after oral administration in rats.

As an example of a method for extracting and obtaining an extract of *Euodia suaveolens* Scheff or oleoresin according to the invention, the steps described below, in particular, are carried out.

The previously dried leaves and flowers of *Euodia suaveolens* Scheff are first coarsely ground.

600 g of non-finely ground plant are thus added to a 20 L three-necked flask placed in a water bath fed with steam.

The extraction is performed with 96% ethanol. Three extractions are performed.

The first extraction is performed with a volume of 10 times the weight of the ground plant, or 6 L. The extraction is carried out under reflux with mechanical stirring for 3 hours, at a temperature of 75° C.

The filtrate is then discharged and collected.

A second extraction is then performed with a volume equal to 6 times the mass of the initial plant, or 3.6 L, under reflux, with stirring for 3 hours.

Thereafter, a final extraction is performed with a volume equal to 4 times the initial mass of plant, that is 2.4 L.

The three filtrates are combined and then filtered on a Büchner filter.

A clear, dark green extract is obtained.

The extract according to the invention is then concentrated under vacuum using a rotary evaporator at a temperature of 60° C.

An oleoresin according to the invention, dark green in color, extracted from *Euodia suaveolens* Scheff, is thus obtained. It has a pasty appearance, is solid at room temperature and viscous-liquid when hot.

The extract according to the invention is then bleached with activated carbon at a content of 10% by weight in an 80/20 ethanol/water mixture. The finally obtained extract according to the invention is reddish/brown, glossy, and soluble in an 80/20 ethanol/water mixture.

The extract according to the invention is moderately fragrant.

Alternatively, the extract according to the present invention is bleached with supercritical $CO_2$.

Various tests using supercritical $CO2$ were carried out on the above oleoresin, for example at a pressure of 180 bar and at a temperature of 45° C., or at a pressure of 250 bar and at a temperature of 45° C., with 10% ethanol as co-solvent.

The $CO_2$ test without a co-solvent results in a lemon yellow, odorous extract, but having a non-uniform appearance.

The $CO_2$ extract obtained with an ethanol-based co-solvent allows a reddish brown, less odorous extract to be obtained.

According to a preferred embodiment, the oleoresin obtained from fresh plants is codistilled on a cosmetically acceptable carrier such as monopropylene glycol. This codistillation provides a pale yellow extract having a high concentration of evodone, for example about 2%.

This extract can then be taken up in hexane to increase the evodone titer.

According to a second aspect, the invention also pertains to a repellent composition comprising, in a cosmetically acceptable medium, evodone at a concentration between 0.1 and 25% by weight of the total weight of the composition.

Preferably, the repellent composition according to the invention comprises evodone at a concentration of between 0.2 and 10% by weight of the total weight of the composition, for example at a concentration of 3% by weight of the total weight of the composition.

The invention also relates to a composition comprising an effective amount of an extract of *Euodia suaveolens* Scheff as defined above, as the active repellent agent against insects, in particular against mosquitoes. It is incorporated into the composition with any cosmetically acceptable excipient. Such a composition is substantially free of any effective amount of linalool, alpha-pinene, evodiamine or rutaecarpine, and, in particular, has an evodone titer, at a concentration of between 0.1 and 25% by weight of the total weight of the composition.

Advantageously, the extract content in the above composition is between 1 and about 70% by weight of the total weight of the composition, preferably 10.10%, 26.8%, 32% or 35%.

For example, a composition according to the invention may comprise 35% of an ethanol extract (ethanol/water as dilution solvent: 80/20), 10.10% of an extract obtained by codistillation with monopropylene glycol, or 26.8% of an extract obtained by alcoholic extraction, formulated with castor oil and ethanol.

The compositions according to the invention may be more or less fluid and may be in any pharmaceutical form suitable for use in a topical application to the skin, for example, in the form of a milk, gel, cream, lotion, emulsion, spray and preferably in the form of a spray.

Examples of solvents used in the composition according to the invention include: water, ethanol, glycerin, propylene glycol, sorbitol.

Said composition may optionally comprise another active ingredient selected from agents which have a recognized repellent effect on insects, preferably a naturally occurring repellent agent, for example menthoglycol or citriodiol.

This naturally occurring agent is derived from the essential oil of *Eucalyptus citriodora*.

By way of illustration, some formulation examples of compositions according to the invention are mentioned below, which contain evodone or the above-mentioned extract of *Euodia suaveolens* Scheff:

EXAMPLE 1

Spray Against European/Mediterranean Mosquitoes (*Aedes aegypti*) for Topical Application 32% of extract of *Euodia suaveolens* Scheff
1.3% of citriodiol
65% of 80%-alcohol
1.7% of monopropylene glycol

EXAMPLE 2

Spray Against European/Mediterranean Mosquitoes (*Aedes aegypti*) for Topical Application 3% of evodone
63% of 100%-alcohol
34% of monopropylene glycol

EXAMPLE 3

Spray Against European/Mediterranean Mosquitoes (*Aedes aegypti*) for Topical Application 26.8% of extract of *Euodia suaveolens* Scheff
33.5% of castor oil
39.7% of 100%-alcohol In a third aspect, the present invention relates to the use of evodone as an active agent for repelling insects, particularly mosquitoes and more particularly European/Mediterranean mosquitoes of the *Aedes aegypti* species.

The invention also relates to the use of an extract of *Euodia suaveolens* Scheff as an active agent, or of compositions as defined above to repel insects, in particular mosquitoes and more particularly European/Mediterranean mosquitoes of the *Aedes aegypti* species.

In this respect, the invention is illustrated by the following efficacy tests, carried out in the laboratory, where the formulas are not degraded through the effects of abrasion, exudation, sunlight, temperature or even swimming in the sea. These tests are designed to demonstrate the repellent effect of evodone and an extract of *Euodia suaveolens* Scheff at different concentrations, purified, whether bleached or not, alone or in combination with another natural active repellent agent such as menthoglycol, on European/Mediterranean mosquitoes of the *Aedes aegypti* species.

The tests are carried out on female *Aedes aegypti* mosquitoes aged 6 to 10 days having undergone a prior 24-hour period of fasting (no blood meal) in order to increase their aggressiveness.

The blood meal target is a mouse of the "hairless" type held in a retaining cage (using eye protection) and coated with the test product (0.1g/60 cm$^2$) applied with a pipette.

30 minutes after product application, the mouse is introduced into a cage containing approximately 200 female mosquitoes (prior removal of the males using a food gradient).

The test lasts 5 minutes and during this period the number of mosquitoes having landed on the mouse ("landing" effect: number of mosquitoes that land on the treated area and leave without biting) and the number of effective bites, are recorded.

The test is stopped after 5 effective bites ("stop" in the Tables below).

The test is repeated with new batches of mosquitoes, at intervals of one hour until a duration of 8 hours is reached, depending on the persistence limit of the product (between the runs, the mouse was released). Based on the outcome of the first repetition, repetitions are performed at time intervals of 30 minutes in order to provide a more accurate limit for the duration of protection.

During and between the runs, the mice are maintained in a "tropical" like atmosphere under controlled conditions at 27+/−1° C. and 70+/−5% relative humidity. The cages are changed upon each unit test and placed 3 meters apart.

3 repetitions are carried out per formula to be tested and on 3 different mice, that is, 9 unit tests per formula.

Test 1:

4 extracts (supplier: Charabot S. A.) are tested comparatively, the solvent serving as a reference (it is verified that at least 10 landings occur in 30 seconds to validate the test):

Extract 1: ethanol extract of *Euodia suaveolens* Scheff according to the invention at a concentration of 35% (ethanol/water as dilution solvent: 80/20) non-bleached;

Extract 2: ethanol extract of Sichuan red pepper (Soxhlet extraction) at a concentration of 19.44% (ethanol as dilution solvent);

Extract 3: ethanol extract at a concentration of 35% of menthoglycol;

Extract 4: Spilanthes extract at a concentration of 18.56% (ethanol as dilution solvent); and Test without any product (reference): solvent.

The results are summarized in the following Table:

| AEDES AEGYPTI | mice | rep. | T0+2H P | L | T0+4H P | L | T0+6H P | L | T0+8H P | L | T0+10H P | L | T0+12H P | L |
|---|---|---|---|---|---|---|---|---|---|---|---|---|---|---|
| Extract 1 | 1 | 1 | 0 | 0 | 0 | 0 | 0 | 3 | stop | stop | stop | stop | stop | stop |
|  |  | 2 | 0 | 0 | 0 | 1 | 0 | 1 | stop | stop | stop | stop | stop | stop |
|  |  | 3 | 0 | 0 | 0 | 1 | 0 | 2 | stop | stop | stop | stop | stop | stop |
|  | 2 | 1 | 0 | 0 | 0 | 0 | 0 | 1 | stop | stop | stop | stop | stop | stop |
|  |  | 2 | 0 | 0 | 0 | 0 | 0 | 2 | stop | stop | stop | stop | stop | stop |
|  |  | 3 | 0 | 0 | 0 | 0 | 0 | 4 | stop | stop | stop | stop | stop | stop |
|  | 3 | 1 | 0 | 0 | 0 | 0 | 0 | 1 | stop | stop | stop | stop | stop | stop |
|  |  | 2 | 0 | 0 | 0 | 1 | 0 | 2 | stop | stop | stop | stop | stop | stop |
|  |  | 3 | 0 | 0 | 0 | 0 | 0 | 0 | stop | stop | stop | stop | stop | stop |
| Extract 2 | 1 | 1 | 0 | 0 | 0 | 1 | stop | stop | stop | stop | stop | stop | stop | stop |
|  |  | 2 | 0 | 0 | 0 | 2 | stop | stop | stop | stop | stop | stop | stop | stop |
|  |  | 3 | 0 | 0 | 0 | 0 | stop | stop | stop | stop | stop | stop | stop | stop |
|  | 2 | 1 | 0 | 0 | 0 | 0 | stop | stop | stop | stop | stop | stop | stop | stop |
|  |  | 2 | 0 | 0 | 0 | 1 | stop | stop | stop | stop | stop | stop | stop | stop |
|  |  | 3 | 0 | 0 | 0 | 0 | stop | stop | stop | stop | stop | stop | stop | stop |
|  | 3 | 1 | 0 | 1 | 0 | 1 | stop | stop | stop | stop | stop | stop | stop | stop |
|  |  | 2 | 0 | 0 | 0 | 1 | stop | stop | stop | stop | stop | stop | stop | stop |
|  |  | 3 | 0 | 0 | 0 | 1 | stop | stop | stop | stop | stop | stop | stop | stop |
| Extract 3 | 1 | 1 | 0 | 0 | 0 | 1 | 0 | 3 | stop | stop | stop | stop | stop | stop |
|  |  | 2 | 0 | 0 | 0 | 1 | 0 | 2 | stop | stop | stop | stop | stop | stop |
|  |  | 3 | 0 | 0 | 0 | 0 | 0 | 2 | stop | stop | stop | stop | stop | stop |
|  | 2 | 1 | 0 | 0 | 0 | 0 | 0 | 0 | stop | stop | stop | stop | stop | stop |
|  |  | 2 | 0 | 0 | 0 | 1 | 0 | 2 | stop | stop | stop | stop | stop | stop |
|  |  | 3 | 0 | 0 | 0 | 0 | 0 | 1 | stop | stop | stop | stop | stop | stop |
|  | 3 | 1 | 0 | 0 | 0 | 0 | 0 | 0 | stop | stop | stop | stop | stop | stop |
|  |  | 2 | 0 | 0 | 0 | 0 | 0 | 1 | stop | stop | stop | stop | stop | stop |
|  |  | 3 | 0 | 0 | 0 | 0 | 0 | 0 | stop | stop | stop | stop | stop | stop |
| Extract 4 | 1 | 1 | 0 | 0 | 0 | 0 | stop | stop | stop | stop | stop | stop | stop | stop |
|  |  | 2 | 0 | 0 | 0 | 1 | stop | stop | stop | stop | stop | stop | stop | stop |
|  |  | 3 | 0 | 0 | 0 | 0 | stop | stop | stop | stop | stop | stop | stop | stop |
|  | 2 | 1 | 0 | 0 | 0 | 1 | stop | stop | stop | stop | stop | stop | stop | stop |
|  |  | 2 | 0 | 0 | 0 | 3 | stop | stop | stop | stop | stop | stop | stop | stop |
|  |  | 3 | 0 | 0 | 0 | 1 | stop | stop | stop | stop | stop | stop | stop | stop |
|  | 3 | 1 | 0 | 1 | 0 | 1 | stop | stop | stop | stop | stop | stop | stop | stop |
|  |  | 2 | 0 | 0 | 0 | 2 | stop | stop | stop | stop | stop | stop | stop | stop |
|  |  | 3 | 0 | 0 | 0 | 1 | stop | stop | stop | stop | stop | stop | stop | stop |

P: number of bites
rep: repetition
L: "landing": number of mosquitoes landing on the treated area without biting
stop = the test is stopped when more than 5 bites have been observed Under these test conditions, with the samples provided, the insect strains and methods considered, extracts 1 and 3 showed a repellent effect against the mosquito, with a persistence of 6 hours after application.

Extracts 2 and 4, at the concentrations used, showed a repellent effect against the mosquito with a persistence of only 4 hours after application.

Extract 1 of *Euodia suaveolens* Scheff, at a concentration of 35%, purified, non-bleached, thus shows a true repellent effect with a persistence of 6 hours against the *Aedes aegypti* mosquito.

Test 2:

3 extracts (supplier: Charabot S. A.) are tested comparatively, with the solvent serving as a reference (it is verified that at least 10 landings occur in 30 seconds to validate the test):

Extract 1: ethanol extract of *Euodia suaveolens* Scheff according to the invention at a concentration of 15%, bleached by molecular distillation (ethanol/water as dilution solvent: 80/20);

Extract 2: ethanol extract of *Euodia suaveolens* Scheff according to the invention, bleached at a concentration of 35% (ethanol/water as dilution solvent: 97%);

Extract 3: menthoglycol (20%)+*Euodia suaveolens* Scheff (15%) mixture (ethanol/water as dilution solvent: 80/20), bleached; and Test without any product (reference): solvent.

The results are summarized in the following Table:

Under these test conditions, with the samples provided, the insect strains and methods considered, extracts 2 and 3 showed a repellent effect against the mosquito, with a persistence of 6 hours after application.

Extract 1 showed a repellent effect against the mosquito, with a persistence of only 4 hours after application.

Extract 2 of *Euodia suaveolens* Scheff, at a concentration of 35%, purified, bleached, and extract 3 comprising a mixture of 20%-menthoglycol and a 15%-extract of bleached *Euodia suaveolens* Scheff, thus show a true repellent effect, with a persistence of 6 hours against the *Aedes aegypti* mosquito.

Test 3:

A test is carried out with 4 compositions according to the invention:

Extract 1: Codistilled extract of *Euodia suaveolens* Scheff, formulated at 0.3% in evodone;

Extract 2: Codistilled extract of *Euodia suaveolens* Scheff, formulated at 2.36% in evodone;

Extract 3: A composition comprising synthetic evodone, formulated at 3%;

Extract 4: Oleoresin of crude, unrefined *Euodia suaveolens* Scheff, formulated at 0.26% in evodone.

Under these test conditions, with the samples provided, and the insect strains and methods considered, the extracts

| AEDES AEGYPTI | mice | rep. | T0 + 2 H | | T0 + 4 H | | T0 + 6 H | | T0 + 8 H | | T0 + 10 H | | T0 + 12 H | |
|---|---|---|---|---|---|---|---|---|---|---|---|---|---|---|
| | | | P | L | P | L | P | L | P | L | P | L | P | L |
| Extract 1 | 1 | 1 | 0 | 0 | 0 | 0 | stop | stop | stop | stop | stop | stop | stop | stop |
| | | 2 | 0 | 0 | 0 | 2 | stop | stop | stop | stop | stop | stop | stop | stop |
| | | 3 | 0 | 0 | 0 | 0 | stop | stop | stop | stop | stop | stop | stop | stop |
| | 2 | 1 | 0 | 0 | 0 | 0 | stop | stop | stop | stop | stop | stop | stop | stop |
| | | 2 | 0 | 0 | 0 | 1 | stop | stop | stop | stop | stop | stop | stop | stop |
| | | 3 | 0 | 0 | 0 | 0 | stop | Stop | stop | stop | stop | stop | stop | stop |
| | 3 | 1 | 0 | 0 | 0 | 0 | stop | Stop | stop | stop | stop | stop | stop | stop |
| | | 2 | 0 | 0 | 0 | 2 | stop | Stop | stop | stop | stop | stop | stop | stop |
| | | 3 | 0 | 0 | 0 | 0 | stop | Stop | stop | stop | stop | stop | stop | stop |
| Extract 2 | 1 | 1 | 0 | 0 | 0 | 0 | 0 | 3 | stop | stop | stop | stop | stop | stop |
| | | 2 | 0 | 0 | 0 | 0 | 0 | 2 | stop | stop | stop | stop | stop | stop |
| | | 3 | 0 | 0 | 0 | 0 | 0 | 0 | stop | stop | stop | stop | stop | stop |
| | 2 | 1 | 0 | 0 | 0 | 0 | 0 | 0 | stop | stop | stop | stop | stop | stop |
| | | 2 | 0 | 0 | 0 | 0 | 0 | 1 | stop | stop | stop | stop | stop | stop |
| | | 3 | 0 | 0 | 0 | 0 | 0 | 0 | stop | stop | stop | stop | stop | stop |
| | 3 | 1 | 0 | 0 | 0 | 1 | 0 | 1 | stop | stop | stop | stop | stop | stop |
| | | 2 | 0 | 0 | 0 | 0 | 0 | 1 | stop | stop | stop | stop | stop | stop |
| | | 3 | 0 | 0 | 0 | 1 | 0 | 2 | stop | stop | stop | stop | stop | stop |
| Extract 3 | 1 | 1 | 0 | 0 | 0 | 0 | 0 | 1 | stop | stop | stop | stop | stop | stop |
| | | 2 | 0 | 0 | 0 | 0 | 0 | 0 | stop | stop | stop | stop | stop | stop |
| | | 3 | 0 | 0 | 0 | 0 | 0 | 0 | stop | stop | stop | stop | stop | stop |
| | 2 | 1 | 0 | 0 | 0 | 0 | 0 | 0 | stop | stop | stop | stop | stop | stop |
| | | 2 | 0 | 0 | 0 | 0 | 0 | 1 | stop | stop | stop | stop | stop | stop |
| | | 3 | 0 | 0 | 0 | 0 | 0 | 1 | stop | stop | stop | stop | stop | stop |
| | 3 | 1 | 0 | 0 | 0 | 0 | 0 | 0 | stop | stop | stop | stop | stop | stop |
| | | 2 | 0 | 0 | 0 | 0 | 0 | 0 | stop | stop | stop | stop | stop | stop |
| | | 3 | 0 | 0 | 0 | 0 | 0 | 0 | stop | stop | stop | stop | stop | stop |
| test without product | 1 | 1 | stop | stop | stop | stop | stop | stop | stop | stop | stop | stop | stop | stop |
| | | 2 | stop | stop | stop | stop | stop | stop | stop | stop | stop | stop | stop | stop |
| | | 3 | stop | stop | stop | stop | stop | stop | stop | stop | stop | stop | stop | stop |
| | 2 | 1 | stop | stop | stop | stop | stop | stop | stop | stop | stop | stop | stop | stop |
| | | 2 | stop | stop | stop | stop | stop | stop | stop | stop | stop | stop | stop | stop |
| | | 3 | stop | stop | stop | stop | stop | stop | stop | stop | stop | stop | stop | stop |
| | 3 | 1 | stop | stop | stop | stop | stop | stop | stop | stop | stop | stop | stop | stop |
| | | 2 | stop | stop | stop | stop | stop | stop | stop | stop | stop | stop | stop | stop |
| | | 3 | stop | stop | stop | stop | stop | stop | stop | stop | stop | stop | stop | stop |

P: number of bites rep: repetition

L: "landing": number of mosquitoes landing on the treated area without biting stop = the test is stopped when more than 5 bites have been observed showed a repellent effect against the mosquito, with the following periods of protection after application:

4 hrs with Extract 1;
6 hrs with Extract 2;
6 hrs with Extract 3;
6 hrs with Extract 4.

A racemic mixture of synthetic evodone formulated at 3% (extract 3) has a repellent activity lasting 6 hours. Evodone can be used as an active agent to repel insects, and particularly mosquitoes. Evodone is responsible, at least in part, for the repellent activity of the extract of *Euodia suaveolens* Scheff according to the invention.

Extract 2 of *Euodia suaveolens* Scheff comprising 2.36% evodone has a more effective repellent activity than extract 1 of *Euodia suaveolens* Scheff comprising 0.3% evodone and obtained under the same conditions by codistillation.

The crude, unrefined oleoresin of *Euodia suaveolens* Scheff, formulated at 0.26% in evodone (extract 4), is as effective as extracts 2 and 3. Evodone is active as such and has a synergistic action in the crude unrefined oleoresin. Evodone may act synergistically in the crude extract according to the invention, with molecules such as other oxygenated terpenes, for instance menthalactone, or non-polar molecules present in the codistilled extracts.

According to the invention, evodone has a repellent activity against mosquitoes. A concentration of 3% or even less of synthetic evodone in extracts of crude or refined *Euodia suaveolens* Scheff is as effective as a concentration of 30% of DEET.

A person skilled in the art will select the cosmetically acceptable medium so that it does not interfere with the desirable properties of the extract and repellent compositions according to the invention.

Of course, the invention is non limited to the embodiments and examples presented above and a person skilled in the art, through routine operations, may need to carry out other embodiments not exclusively described here, that broadly fall within the scope of the invention.

The invention claimed is:

1. A method of repelling insects, comprising applying an effective amount of an insect-repellant composition comprising evodone to an area in need of being protected from insects,
   wherein the composition comprises the evodone at a concentration of between 0.8 and 35% by weight,
   wherein the composition comprises at least one of linalool, alpha-pinene, evodiamine and rutaecapine.

2. The method according to claim 1, wherein the evodone is synthetic evodone.

3. The method according to claim 2, wherein the evodone is synthesized from 5-methylcyclohexan-1,3-dione in the presence of chloroacetone.

4. The method according to claim 1, wherein the composition comprises evodone at a concentration of between 2% and 20% by weight of the total weight of the composition.

5. The method according to claim 1, wherein the composition comprises evodone at a concentration of between 2% and 10% by weight of the total weight of the composition.

6. The method according to claim 1, wherein the composition comprises evodone at a concentration of between 2% and 5% by weight of the total weight of the composition.

7. The method according to claim 1, wherein the composition comprises evodone at a concentration of about 3% by weight of the total weight of the composition.

8. The method according to claim 1, wherein the insects are mosquitoes.

9. The method according to claim 8, wherein the mosquitoes are the European/Mediterranean mosquitoes of the *Aedes aegypti* species.

10. The method according to claim 1, wherein the composition comprises at least one of linalool, alpha-pinene, evodiamine and rutaecapine at a concentration of less than 0.1% by weight of the total weight of the composition.

11. The method according to claim 10, wherein the composition does not comprise any of linalool, alpha-pinene, evodiamine and rutaecapine at a concentration of more than 0.1% of the total weight of the composition.

12. The method according to claim 1, wherein the composition comprises evodone at a concentration of between 0.8% and 25% by weight, and wherein the composition further comprises a cosmetically-acceptable vehicle selected from the group consisting of water, ethanol, glycerin, propylene glycol, sorbitol, alcohol, and monopropylene glycol.

13. The method according to claim 12, wherein the composition comprises evodone at a concentration of between 2% and 10% by weight of the total weight of the composition.

14. The method according to claim 13, wherein the composition comprises evodone at a concentration of between 2% and 5% by weight of the total weight of the composition.

15. The method according to claim 14, wherein the composition comprises evodone at a concentration of about 3% by weight of the total weight of the composition.

16. The method according to claim 12, wherein the insects are mosquitoes.

17. The method according to claim 16, wherein the mosquitoes are the European/Mediterranean mosquitoes of the *Aedes aegypti* species.

18. The method according to claim 1, wherein the composition is applied on at least one of clothing and human skin.

19. The method according to claim 12, wherein the composition is coated by topical application on an area to be protected from insects.

20. The method according to claim 19, wherein the composition is coated on at least one of clothing and human skin.

21. The method according to claim 12, wherein the composition is sprayed by topical application on an area to be protected from insects.

22. The method according to claim 21, wherein the composition is sprayed on at least one of clothing and human skin.

* * * * *